United States Patent [19]

Carrell et al.

[11] Patent Number: 4,944,728
[45] Date of Patent: Jul. 31, 1990

[54] INTRAVENOUS CATHETER PLACEMENT DEVICE

[75] Inventors: Michael W. Carrell; Stephen H. Gericke, both of Oklahoma City, Okla.

[73] Assignee: Safe Medical Devices, Inc., Moore, Okla.

[21] Appl. No.: 258,578

[22] Filed: Oct. 17, 1988

[51] Int. Cl.$^5$ .............................................. A61M 5/00
[52] U.S. Cl. ................................... 604/164; 604/168; 604/110; 604/263
[58] Field of Search ........ 604/110, 158, 162, 164–168, 604/192, 198, 263, 169

[56] References Cited

U.S. PATENT DOCUMENTS

| | | | |
|---|---|---|---|
| 3,536,073 | 10/1970 | Farb | 604/162 |
| 3,585,986 | 6/1971 | Krug | 604/165 |
| 3,640,278 | 2/1972 | Friedman | 604/192 |
| 3,895,632 | 7/1975 | Plowiecki | 604/169 |
| 4,096,860 | 6/1978 | McLaughlin | 604/167 |
| 4,160,450 | 7/1979 | Doherty | 604/162 |
| 4,464,171 | 8/1984 | Garwin | 604/53 |
| 4,525,157 | 6/1985 | Vaillancourt | 604/165 |
| 4,643,200 | 2/1987 | Jennings, Jr. | 604/198 |
| 4,660,570 | 4/1987 | Dombrowski | 604/198 |
| 4,668,226 | 5/1987 | Omata et al. | 604/164 |
| 4,676,783 | 6/1987 | Jagger et al. | 604/162 |
| 4,681,567 | 7/1987 | Masters et al. | 604/198 |
| 4,723,943 | 2/1988 | Spencer | 604/198 |
| 4,747,831 | 5/1988 | Kulli | 604/198 |
| 4,752,290 | 6/1988 | Schramm | 604/263 |
| 4,762,516 | 8/1988 | Luther et al. | 604/110 |
| 4,772,265 | 9/1988 | Walter | 604/164 |
| 4,832,696 | 5/1989 | Luther et al. | 604/164 |
| 4,834,718 | 5/1989 | McDonald | 604/164 |
| 4,846,805 | 7/1989 | Sitar | 604/110 |
| 4,850,961 | 7/1989 | Wanderer et al. | 604/110 |

Primary Examiner—Stephen C. Pellegrino
Assistant Examiner—Ralph Lewis
Attorney, Agent, or Firm—Laney, Dougherty, Hessin & Beavers

[57] ABSTRACT

An intravenous catheter placement device which includes a tubular catheter section concentrically surrounding an elongated tubular needle which has a bias cut point projecting from one end of the catheter section with the bias cut point of the needle being used to lead the catheter section into a blood vessel. A protective sheath subassembly is connected to the needle and to the catheter section to permit the needle to be withdrawn through the tubular catheter section into a protective rigid tubular sheath, leaving the catheter section emplaced in the blood vessel. Locking elements on the protective tubular sheath subassembly lock the needle in the protected position.

16 Claims, 2 Drawing Sheets

INTRAVENOUS CATHETER PLACEMENT DEVICE

FIELD OF THE INVENTION

This invention relates to an intravenous catheter placement device for quickly, efficiently and safely emplacing an intravenous catheter tip into a blood vessel to permit intravenous injection of nutrients and medicaments.

BACKGROUND OF THE INVENTION
BRIEF DESCRIPTION OF THE PRIOR ART

It is frequently difficult to quickly, efficiently and safely emplace intravenous catheters so that the tip of the catheter is inserted in the blood vessel in a way which does not damage the vessel or surrounding tissues, and which permits an intravenous introduction of fluid to the blood vessel immediately thereafter. Moreover, where a needle is used to puncture the blood vessel in advance of the catheter tip entering through the opening made by the needle, retraction of the needle to leave the catheter in position frequently poses the possibility of the nurse or paramedic placing the catheter being scratched or nicked by the needle. Further, retraction of the needle sometimes causes the catheter end itself to be pulled back out of the blood vessel. Moreover, disposition of such needle in a safe mode so that it is beyond any possibility of re-use or inadvertent scratching of personnel is a desiderata very imperfectly realized with present systems for emplacing intravenous catheters.

BRIEF DESCRIPTION OF THE PRESENT INVENTION

The present invention provides a device for emplacement of an intravenous catheter so that the tip of the catheter is easily inserted in a blood vessel into which an I.V. solution, either as a nutrient or as a medicament, is to be introduced. The system or device permits the catheter to be very quickly and safely placed in the blood vessel in a way that is essentially foolproof and error free.

The catheter emplacement device of the invention provides increased patient and user safety by completely enclosing the insertion needle in a crush proof container after the needle has been used at the cathteter insertion site. The needle is prevented by a locking mechanism from being re-introduced into the blood vessel of the patient, or into the catheter after the catheter has been emplaced. The latter feature of the device is an important characteristic because it precludes the possibility of the needle scraping the wall of the plastic catheter and causing bits of plastic to enter the blood vessel and act as sites for the formation of emboli.

Broadly described, the intravenous catheter emplacement device of the invention includes an elongated tubular catheter section which concentrically surrounds, and slidably engages, an elongated tubular needle having a sharpened point at one end. A beveled or tapered end is carried on the catheter section and is spaced along the needle from the sharpened point. A protective sheath subassembly is connected to the needle and to the catheter section and functions to permit the needle to be retracted through the tubular catheter section while the catheter section is maintained in position within the blood vessel.

The retraction of the needle is continued until it is withdrawn into a protective rigid tubular sheath subassembly immediately after it passes from the catheter section. The protective sheath subassembly is then disengaged from the catheter section which will normally carry a hub, collar or other socket element at the end thereof opposite its end within the blood vessel. A catheter tube can then be easily connected to such hub or collar. Locking elements are provided on the protective tubular sheath subassembly for the purpose of locking the needle in its protected position within the protective tubular sheath which forms a part of the sheath subassembly. A linear ratchet device is also provided and functions during retraction of the needle to prevent reverse movement of the needle in a direction toward the catheter section and blood vessel. This prevents the needle from "shaving" particles of plastic off of the catheter with consequent risk of them entering the blood vessel.

An important object of the invention is to permit the emplacement of an intravenous catheter within a blood vessel so that the needle used to open the blood vessel to receive the catheter tip is immediately thereafter safely retracted through the tubular catheter section and into a contiguous protective tubular sheath.

Another object is to provide a sheath subassembly by which a needle used to emplace a catheter in a blood vessel can be effectively withdrawn in a straight and true fashion which does not damage the blood vessel, nor cause particles of plastic or synthetic resin from the catheter section to be scraped away by the needle, and allowed to enter the blood stream to constitute emboli formation situses.

A further object of the invention is to provide a means for safely disposing of a tubular needle element used for emplacing an intravenous catheter in a blood vessel following a time when the catheter is emplaced.

A further object of the invention is to provide an intravenous catheter emplacement device which is easy to utilize and requires no special training of long duration to permit a person to use it effectively and safely.

A further object of the invention is to assure that during the use of the intravenous catheter device of the invention, all of the blood "flash" developed to indicate proper needle insertion is contained within a crush proof container. Thus, personnel contact with the blood of the patient is minimized.

Another object of the invention is to provide a catheter emplacement device which is constructed so as to protect the user from accidental self-inflicted needle contact during use by causing the needle forming a part of the device to be locked inside a crush proof sheath immediately following use.

Additional objects and advantages of the invention will become apparent as the following detailed description of the invention is read in conjunction with the accompanying drawings which illustrate the invention.

DETAILED DESCRIPTION OF PREFERRED EMBODIMENTS OF THE INVENTION

Figures 1, 2, 2A, 3, 4:
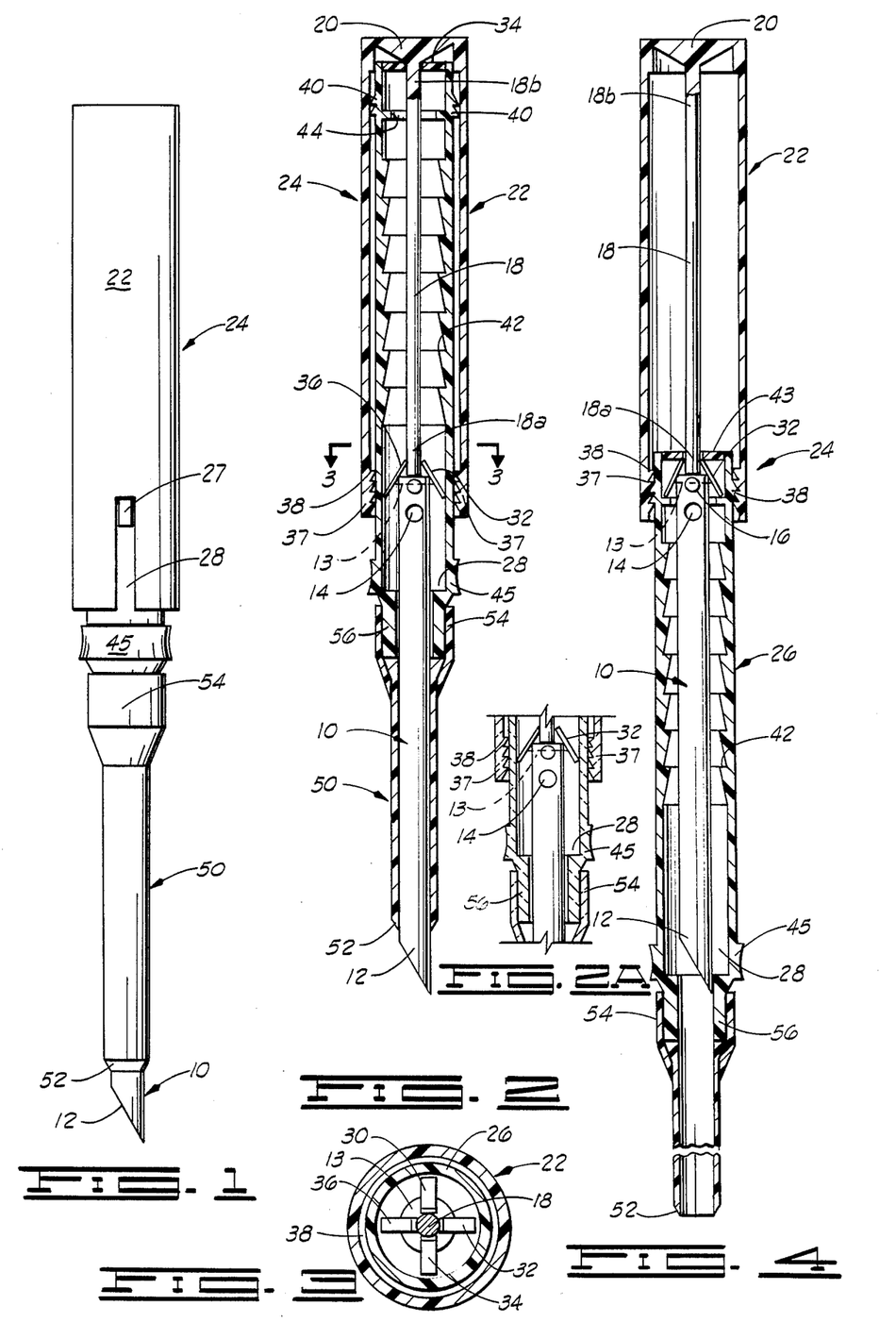
FIG. 1 is a view in side elevation of a safe intravenous catheter placement device constructed in accordance with the present invention. The catheter placement device is illustrated in the status it assumes at the time when the catheter tip is to be emplaced in a blood vessel.
FIG. 2 is a longitudinal sectional view taken along the center line of the intravenous catheter placement device shown in FIG. 1, but illustrating in elevation a tubular needle and needle retraction rod.
FIG. 2A is a view in section of a structural detail illustrating the transparent characteristic of certain parts of the intravenous cathetor placement device as they are constructed of a transparent material in a preferred embodiment of the invention.
FIG. 3 is a sectional view taken along line 3—3 of FIG. 2.
FIG. 4 is a sectional view similar to FIG. 2, but illustrating the catheter placement device after the tubular needle has been retracted through an intravenous catheter section and into a protective tubular sheath following insertion of the tubular catheter section into a blood vessel.

Referring initially to FIG. 1 of the drawings, an elongated hollow needle 10 has a sharpened point 12 which is cut on a bias. The plane of the cut extends at an angle of from about 30° to about 45° to the longitudinal axis of the needle. At its end opposite the tip 12, the needle 10 is closed by a transverse plate 13, and is provided with a plurality of radially opening flash ports 14 and 16 near the end of the needle.

An elongated rod 18 which, in the illustrated embodiment, is constructed of plastic, has one of its ends 18a connected to the internal end of the needle 10 adjacent the transverse closure plate 13, and has its second end 18b connected to a top plate 20 of an external box or tubular sheath, designated generally by reference numeral 22. The external sheath 22 forms a part of a sheath subassembly, denominated generally by reference numeral 24. The sheath subassembly 24 includes, in addition to the external sheath 22, an internal box or tubular sheath 26 of the configuration best illustrated in FIG. 4.

At its end which is nearest to the pointed end of the needle and the catheter end section, the internal tubular sheath 26 carries a cylindrical end portion 55 as shown in FIG. 4.

As will be apparent when reference is made to FIGS. 2, 3 and 4, the external tubular sheath 22 surrounds the tubular internal sheath 26 and is slidably movable in an axial reciprocating or telescoping motion relative thereto, so that the external sheath can move from the position illustrated in FIG. 2 to the position illustrated in FIG. 4. The internal sheath 26 carries a radially protuberant key 27 which projects into an axially extending keyway slot 28 as shown in FIG. 1. This prevents relative rotative movement of the two sheaths and of the needle 10 about the longitudinal axes of the sheaths and the needle during the first portion of the needle's retractive movement. The needle is therefore prevented from rotating within the blood vessel, and deleteriously incising the wall of the vessel. Moreover, the cylindrical configuration of the sheath subassembly 24, and specifically the outer or external tubular sheath 22, allows the two sheaths 22 and 26 to be rotated concurrently in the fingers of the physician or technician to selectively adjust the angle of attack of the needle point as may be optimum. It will be understood that in some injection procedures, it would be awkward and difficult to attempt to insert the needle point into a blood vessel without adjustment of the angle of attack of the point in relation to the blood vessel, and in relation to the location of the blood vessel on the body. In a preferred construction of the invention, the inner tubular sheath 26 is constructed of a transparent or translucent plastic material (see FIG. 2A) so that the "flash" of blood occurring at the time that the sharpened tip 12 of the needle 10 forced into a blood vessel can be easily seen. This aspect of the invention will be subsequently explained in greater detail.

Adjacent its end 18a connected to the internal end of the needle 10, the elongated shaft or rod 18 carries a plurality of radially outwardly extending, axially inclined, spring metal locking fingers or detent elements. In the illustrated embodiment of the invention, four of these locking fingers are illustrated, and are denominated by reference numerals 30, 32, 34 and 36 (see FIG. 3). The length of the locking fingers 30-36 is such that these fingers bear resiliently against the inner wall of the inner tubular sheath 26, as illustrated in FIG. 2 of the drawings.

It will be noted that at the location where its one end is closest to the needle 10, the outer tubular sheath carries an integrally formed internally serrated sleeve 37 which defines a plurality of saw tooth annular jam rings or ridges 38 which, in the illustrated embodiment, extend concentrically around the inner tubular sheath 26 and bear against the outer surface thereof. The ridges 38 are configured to be complementary to a series of annular jam rings or ridges 40 formed at the upper end of the inner tubular sheath 26 so that these ridges interfit or interlock in the manner illustrated in FIG. 4 for a purpose and at a time hereinafter described.

It will also be noted in referring to FIGS. 2 and 4 that the inner tubular sheath 26 carries a plurality of axially facing radial shoulders 42 which face away from the point 12 of the needle 10. These shoulders collectively form a linear ratchet which interacts or cooperates with the locking fingers 30-36 in order to prevent the movement of the outer sheath 22 along the inner sheath 26 in a reverse direction so as to extend the needle out of the inner sheath once it has been retracted thereinto after a time when an intravenous catheter has been placed in the blood vessel. It is important that the needle 10 not move back into the plastic catheter section, hereinafter described, because such movement can scrape or shave plastic particles from the catheter section. These particles can then enter the blood vessel and act as sites around which dangerous emboli can form.

The tubular inner sheath 26 has a stop plate 43 at its upper end, with a central aperture formed through the stop plate to accommodate the shaft or rod 18. The tubular inner sheath 26 also carries a centrally apertured annular locking plate or flange 44 extending around the inside of the inner sheath 26. The locking flange 44 is spaced axially inwardly in the inner sheath from the stop plate 43 by a distance adequate to permit the locking fingers 30–36 to pass by the locking flange 44 and then spring radially outwardly to the position illustrated in FIG. 4. At its lower end, the inner tubular sheath 26 carries an annular finger gripping ring 45 which extends around the outside of the inner tubular sheath, and allows it to be held stationary at a time when the outer tubular sheath is retracted in a reciprocating motion in an axial direction relative to the inner sheath. The gripping ring 45 has a convex surface at its outer side as shown in FIGS. 1 and 4.

The needle 10 extends through a tubular intravenous catheter end section designated generally by reference numeral 50. The intravenous catheter end section 50 has a beveled end or tip 52 disposed adjacent the sharpened point 12 of the needle 10, and has a diameter such that it snugly concentrically surrounds the needle as shown in FIGS. 1 and 2. At its end opposite the beveled tip 52, the tubular catheter section 50 carries a cylindrical collar 54 into which is pressed the cylindrical end portion 55 of the inner tubular sheath 26.

The construction and relative arrangement of the needle 10 and intravenous catheter end section 50 are such that the needle 10 may be retracted or extricated through the catheter section so as to leave the beveled tip 52 of the catheter end section 50 inserted in a blood vessel which has been pierced by the sharpened tip 12 of the needle. After the needle has been withdrawn through the catheter section, the inner tubular sheath 26 can be disconnected from the hub or collar 54 of the catheter section, and a tube extending to an intravenous feeding reservoir or bottle can be connected to the catheter end section by pressing an end of such tube into the collar 54.

As shown in FIG. 2A of the drawings, the outer tubular sheath 22 and the inner tubular sheath 26 can be constructed of a transparent material, such as clear plastic. The transparent material shown in FIG. 2A of the drawings can, in one embodiment of the invention, be used to construct all of the remaining portion of the intravenous catheter placement device, except the needle 10.

OPERATION

At a time when it is desired to emplace an intravenous catheter in a blood vessel for the purpose of intravenous feeding, or introduction of a medicament into the blood stream, the tubular needle 10 is first introduced into a blood vessel in the same way that a hypodermic needle carried on a syringe is so introduced. Thus, the sharpened point 12 is pushed very slowly through the wall of the blood vessel so as not to penetrate the opposed blood vessel wall by passing completely through the vessel.

After the point 12 of the needle 10 has entered the blood vessel, a flash of blood is perceived in the end portion or flash chamber 28 of the inner tubular sheath 26. The show of blood or flash within the flash chamber 28 occurs as blood enters the point 12 of the needle and moves through the needle to the locus of the radial ports 14 and 16 in the inner end portion of the needle. The blood from the ports 14 and 16 which has entered the flash chamber 28 can be easily perceived through the transparent inner sheath 26.

Having thus gained the visual assurance that the point 12 of the needle 10 is properly placed within the blood vessel, the nurse or physician emplacing the catheter can then force the point 12 of the needle slightly further into the blood vessel very slowly and gradually, while at the same time, forcing the beveled tip 52 of the intravenous catheter section 50 into the blood vessel. When this has occurred so that the beveled tip 52 is very slightly within the blood vessel, the needle 10 is retracted through the catheter end section to leave the catheter section in place in the blood vessel. Retraction of the needle 10 through the catheter section is accomplished by reciprocating the external, tubular sheath 22 relative to the internal tubular sheath 26 while holding the inner tubular sheath and catheter section stationary by gripping the gripping ring 45. The direction of relative movement is such that the external sheath 22 slides outwardly on the internal sheath 26 toward the position illustrated in FIG. 4 of the drawings. This movement of the external sheath 22 causes the needle 10 to be retracted through the catheter end section 50 and into the internal tubular sheath 26. The retraction of the needle 10 continues until the sharpened tip 12 is housed within the tubular sheath 26, and is thus protectively enclosed as shown in FIG. 4 of the drawings.

As pointed out above, during the retraction of the needle 10 through the catheter end section 50 and into the tubular internal sheath 26, the internal sheath is retained in a fixed position relative to the catheter end section 50, and the blood vessel in which the end thereof is located, by means of the concavely cross-sectioned finger gripping ring or collar 44.

As the outer or external sheath 22 is reciprocated toward the position depicted in FIG. 4, the fingers 30–36 slide past the several shoulders 42 forming the linear ratchet on the internal wall of the internal tubular sheath 26, springing radially outwardly after each shoulder is passed. This assures that it is not possible, after the fingers 30–36 pass any shoulder, to cause the outer or external sheath 22 to reciprocate in the opposite direction so as to again cause the point 12 of the needle 10 to move toward the arm of the patient, or to an exposed position outside the inner tubular sheath 26.

Ultimately, during the retractive movement of the needle 10, the spring fingers 30–36 will spring outwardly after passing the locking flange 44 and will, upon spreading apart from each other, engage the locking flange 44 in a way which prevents the elongated rod 18 and the needle 10 from being reciprocated in a reverse direction which would result in the exposure of the sharpened point 12 of the needle 10. It will also be perceived that at this time, the ribs or ridges 38 are interlocked with the annular locking ribs 40 carried on the outer periphery of the inner tubular sheath 22, so that no movement of the needle outwardly through the top or upper end of the inner tubular sheath 26 can occur. In fact, at this point, relative movement of the two sheaths 22 and 26 by movement of either, in either direction, is prevented by the type of interlocks which are provided and which have been described.

A modified or second embodiment of the invention is illustrated in FIGS. 5–9. There is again provided, in this embodiment, an elongated, tubular needle 56 which carries a sharpened end 58. The needle 56 has a closed second end 60 adjacent a plurality of radially opening ports 62, 64 and 66 formed in the tubular needle 56, and communicating the bore or axial passageway through the needle with the outside of the needle.

Figures 5, 6, 7, 8, 9, 10:
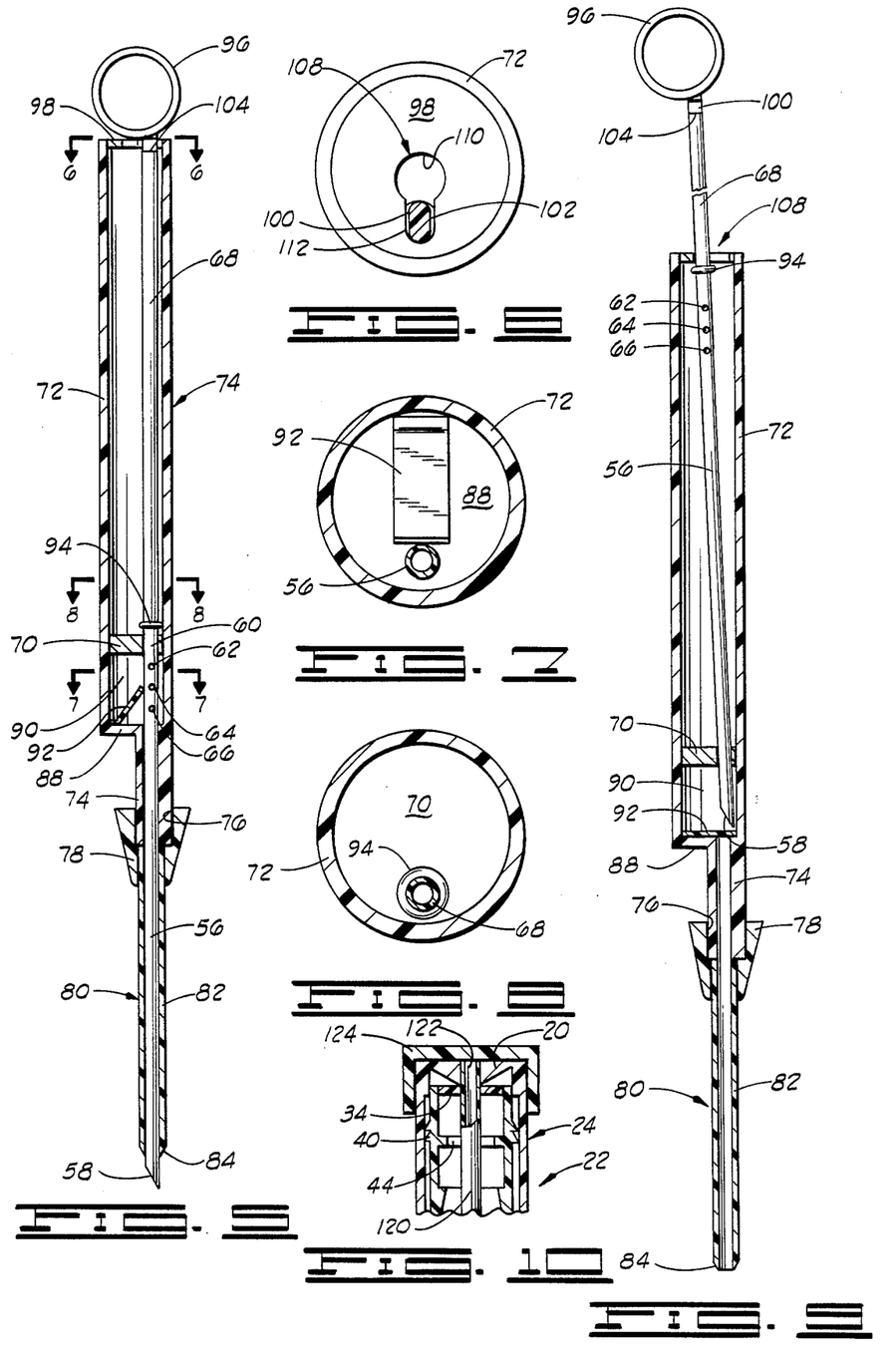
FIG. 5 is longitudinal sectional view through the central longitudinal axis of a second embodiment of the intravenous catheter placement device illustrating the needle, needle retraction rod and finger ring or handle in elevation.
FIG. 6 is a sectional view taken along line 6—6 of FIG. 5.
FIG. 7 is a sectional view taken along line 7—7 of FIG. 5.
FIG. 8 is a sectional view taken along line 8—8 of FIG. 5.
FIG. 9 is a sectional view similar to FIG. 5, but illustrating the appearance of the second embodiment of the intravenous catheter placement device as it appears after the needle has been withdrawn into a safe position within a tubular sheath.
FIG. 10 is a sectional view illustrating a modified structure which is included in yet a different embodiment of the invention.

At its closed end 60 opposite the point 58, the needle 56 is attached to an elongated rod or shaft 68 which is solid. The shaft 68 extends slidably through an aperture formed in a partition plate 70. The partition plate 70 extends transversely across, and partitions off, a flash chamber, hereinafter described, in one end portion of an elongated hollow barrel 72. The barrel 72 forms a portion of a protective tubular sheath subassembly designated generally by reference numeral 74. The barrel 72 is secured at its end closest to the point 58 of the needle 56 to a tubular sleeve or neck 75 which forms a cylindrical end portion of the tubular sheath subassembly 74. The sleeve or neck 75 is pressed into a cylindrical recess 76 which is formed in the enlarged end portion of a conically-shaped collar 78 which forms one end of a tubular intravenous catheter end section designated generally by reference numeral 80. The catheter end section 80 includes, in addition to the collar 78, an elongated tube 82 which terminates in a beveled end or tip 84 located adjacent the sharpened point 58 of the needle 56.

It will be perceived in referring to FIG. 5 that the partition plate 70 forms, with an end plate 88 which is located at the intersection of the barrel 72 with the sheath subassembly 74, a flash chamber 90. The flash chamber 90 is generally cylindrical in configuration, and encloses a flapper valve 92, the flapper valve 92 is a flat plate which, by reason of its inherent resiliency, will spring to a closed position, as shown in FIG. 9 when the needle 10 is retracted past this plate. In this closed position it will lie across and close the opened end of the passageway through the tubular sleeve 75 of the sheath subassembly.

At a location immediately above the partition plate 70, the elongated shaft 68 carries an annular rib 94. The purpose of the annular rib will be hereinafter explained. At its upper end, the elongated shaft 68 is connected to a finger ring 96 which lies outside of the hollow barrel 72 and beyond a barrel closure plate 98. It will be perceived in referring to FIGS. 1 and 6 that the shaft 68 is provided near its upper end, where it is joined to the finger ring 96, with a pair of opposed recesses which terminate at flat surfaces 100 and 102 on opposite sides of the shaft. The recesses are best illustrated in FIGS. 5 and 6. In FIG. 6 it will be noted that the effect of the recessing of the shaft on opposite sides thereof to form the flat surfaces 100 and 102 is to also form a pair of shoulders 104 and 106 which are located on opposite sides of the shaft adjacent the flat surfaces.

In FIG. 6 it will be noted that the closure plate 98 defines a key hole-shaped aperture 108. The aperture 108 includes a circular portion 114 disposed relatively near to the center of the plate, and a narrow eliptical portion 110 disposed adjacent one side of the plate. The width of the eliptical portion 110 of the slot is such that when the shaft 68 is pulled to one side of the plate, the restricted or narrowed neck of the shaft carrying the surfaces 100 and 102 can be fitted into the eliptical portion 110 of the slot 112, and the shoulders 104 and 106 will prevent the shaft from moving upwardly relative to the closure plate 98.

In utilizing the modified embodiment of the invention shown in FIGS. 5-9, the elongated tubular needle 56 is initially used to penetrate the blood vessel into which the intravenous catheter is to be placed. As previously explained, the sharpened tip 58 of the needle 56 is slowly pressed through one side of the blood vessel, at which time there is an instantaneous flash of blood in the flash chamber 90. As the blood flows through the tubular needle 56 and out the radial ports 62, 64 and 66, the user of the device then pushes the needle very slowly and slightly further into the blood vessel, so as to emplace the beveled tip of the intravenous catheter end section 80 in the blood vessel.

After this, the person carrying out the procedure then firmly grips the tubular sleeve 75 at the location of the flash chamber 90, and begins to slowly extricate the needle 56 from the blood vessel and through the catheter end section 80. This is accomplished by gripping the finger ring 96 and commencing to pull the needle 56 into the catheter section by means of the elongated shaft 68 which is connected between the finger ring and the needle.

It will be noted that prior to the time the needle is to be retracted through the catheter end section 80, the needle cannot be caused to back away from the blood vessel or move up inside the catheter due to pressure applied to the sharpened end of the needle. This is because at this time the shaft 68 is interlocked in the key hole-shaped opening 108 formed in the closure plate 98 in the manner shown in FIG. 6. Thus, at this time, the opposed shoulders 104 and 106 formed on the shaft will not pass through the eliptical portion 110 of the key hole-shaped opening and the needle cannot be forced into the catheter section.

It will further be noted that at this time the flat surfaces 100 and 102 on opposite sides of the shaft 68 adjacent the finger ring 96 prevent the shaft from undergoing rotation about its longitudinal axis, since these flat surfaces are closely adjacent the opposed side edges of the relatively narrow eliptical portion 110 of the key hole-shaped opening 108. The importance of this construction and this function is that the needle 56, to which the shaft 68 is secured, cannot rotate about its axis at a time when the sharpened point 58 of the needle is in the blood vessel. The sharpened point 58 is thus prevented from gouging through the blood vessel, or scraping the sides of the blood vessel due to any such undesirable rotation of the needle about its longitudinal axis.

When the person carrying out the procedure desires to retract the needle 56, the finger ring 96 is used to move the shaft 68 outwardly from the eliptical portion 110 of the key hole-shaped opening 108 and into the circular portion 114. The circular portion 114 of the key hole-shaped opening 108 is sufficiently large to permit the shaft 68 to reciprocate through this opening as the shaft is pulled outwardly relative to the barrel 72. This outward movement of the shaft 68 causes the needle 56 to be retracted through the elongated intravenous catheter end section 80. Ultimately, the needle point bypasses the flapper valve 92 which, by reason of its spring loading, then springs downwardly to close the opening into the flash chamber 90.

At this time, the annular rib 94 carried on the shaft 68 just above the openings 62, 64 and 66 at the upper end of the needle 56 will be immediately beneath the circular portion 114 of the key hole-shaped opening 108 in the closure plate 98. Therefore, the shaft 68 cannot be pulled further upwardly at this time, and the needle is therefore locked in the position illustrated in FIG. 9 of the drawings. It will be here perceived that the sharpened point 52 of the needle 56 is protected within the flash chamber 90, and due to the canting of the needle and rod or shaft relative to the axis of the barrel 72 in the manner shown in FIG. 9, the sharpened point 58 of the needle cannot move back down through the passageway formed in the tubular neck 75 and the catheter section 80 so as to again project dangerously from the end of the catheter section. In fact, the point of the needle is prevented from leaving the tubular sleeve or sheath at all at this time. Thus, it is protected against inadvertent contact or unauthorized re-use. When the needle has been retracted to the position shown in FIG. 9, the tubular sleeve or neck 75 of the tubular sheath is pulled out away from the catheter end section so that the socket or cylindrical recess 76 formed in the conically-shaped collar is opened, and is ready to receive an elongated medial section of catheter which can be connected to an I.V. bottle or the like.

FIG. 10 illustrates a portion of a third embodiment of the present invention. The structural modification entailed is shown in a device which is generally of the type shown in FIGS. 1-4 of the drawings. Identical reference numerals have been used to identify parts which are identical in FIG. 10 to the same parts shown in the embodiment of the invention in FIGS. 1-4. In FIG. 10, the elongated shaft or rod which is connected to the hollow or tubular needle at one of its ends is also tubular, and is here designated by reference numeral 120. The bore or passageway through the tubular rod 120 is designated by reference numeral 122 and opens through the closure cap 20 which closes the upper end of the outer tubular sheath 24. A friction cap 124 is pressed over the end of the outer tubular sheath 24, and against the planar end surface of the closure plate 20. The friction cap 124 closes the bore 122 through the tubular rod 120 when the cap is in place over the end of the outer tubular sheath. The friction cap 124 can be removed by twisting it off of the end of the outer tubular sheath 24.

In the embodiment of the invention which includes the modified end portion as shown in FIG. 10, the intravenous catheter placement device is used in the same way as the embodiment depicted in FIGS. 1 and 4 is used, and as has been hereinbefore described, for emplacing the catheter. It is possible with the embodiment modified as shown in FIG. 10, however, to remove the friction cap 124 in order to enable the physician, or attending person, to have access to the interior of the blood vessel through the elongated tubular rod or shaft 120 which communicates with the passageway or bore through the tubular needle 10. Thus, in some instances, it may be desirable for various reasons, for example, to extend an elongated stainless steel wire or an elongated probe of some type through the tubular rod 120, the tubular needle 10 and into the blood vessel via the catheter 84 or, even prior to that time, via the tip 12 of the needle 10. In either case, the removable friction cap 124 and the hollow or tubular rod or shaft 120 facilitate such procedure.

Although a preferred embodiment has been herein described, it will be understood that various changes and innovations in the described structures can be made without departure from the basic principles of the invention. Changes and innovations of this type are therefore deemed to be circumscribed by the spirit and scope of the invention except as the same may be necessarily limited by the appended claims or reasonable equivalents thereof.

What is claimed is:

1. A safe intravenous catheter placement device comprising:

an elongated, tubular needle having a hollow interior and having a sharpened, pointed first end and a second end, said tubular needle having a plurality of radial blood flash ports extending radially through the wall of said needle at a location nearer to said second end of said needle than to said first end of said needle for discharging out through said radial flash ports, blood passing through said needle from a blood vessel;

a tubular intravenous catheter end section positioned concentrically around a portion of said needle and including:

a first end adjacent the sharpened point at said first end of said needle and slidably encircling the outer periphery of the needle; and an open, second end;

a protective sheath subassembly around a portion of said needle, which portion of said needle is located between the first end thereof and the second end thereof, and includes the second end thereof, said protective sheath subassembly comprising:

an elongated, tubular sheath which includes at the end thereof closest to the pointed first end of said needle, a transparent cylindrical end portion encircling the medial portion of said needle between the ends of said needle and removably connected to the open second end of said catheter end section, said tubular sheath further including a blood-receiving flash chamber surrounding the portion of said needle having said radial blood flash ports therethrough, said flash chamber being located adjacent said transparent cylindrical end portion, said elongated tubular sheath surrounding a portion of said needle which is spaced therealong from said pointed first end of said needle; and manual retracting means connected to said second end of said needle for retracting said needle through said catheter end section and said transparent cylindrical end portion, and into said tubular sheath so that said pointed first end of said needle is within said tubular sheath, said manual retracting means comprising:

an elongated tubular shaft having one of its ends connected to the second end of said tubular needle and defining a passageway communicating with the hollow interior of the needle; and handle means connected to said elongated tubular shaft and including removable cap means selectively closing said tubular shaft at its end opposite its end connected to the second end of said needle; and means for locking said needle in a retracted, protected position in which said pointed first end is within, and is protected by, said elongated tubular sheath.

2. A safe intravenous catheter placement device as defined in claim 1 wherein said handle means comprises a second tubular sheath slidably surrounding said first mentioned tubular sheath and joined to said elongated tubular shaft.

3. A safe intravenous catheter placement device as defined in claim 2 and further characterized as including means axially keying said tubular sheaths to each other to permit axial relative movement therebetween while preventing rotational movement of one sheath relative to the other sheath about the common axes thereof.

4. A safe intravenous catheter placement device as defined in claim 1 and further characterized as including means for preventing said needle from rotating about its axis and relative to said tubular sheath and said catheter end section prior to a time when said pointed end of the needle is retracted into said catheter end section.

5. A safe intravenous catheter placement device comprising:

an elongated tubular hypodermic needle having a point at a sharpened first end thereof and having a second end;

a tubular intravenous catheter section positioned concentrically around said hypodermic needle and including a first end portion adjacent the tip of the hypodermic needle and snugly encircling the outer periphery of the needle, and further including an open second end; and a protective sheath subassembly connected to the second end of said needle and the second end of said catheter section, said sheath subassembly comprising:

a first tubular sheath;

a second tubular sheath concentrically positioned with respect to said first tubular sheath, and slidably movable in an axial direction relative to said first tubular sheath;

one of said tubular sheaths having an end connected to said open second end of said catheter section;

a connecting element interconnecting the other of said tubular sheaths to the second end of said needle for drawing said needle in one direction through said catheter section and into the interior of said one tubular sheath when said tubular sheaths are displaced in an axial direction relative to each other; and a plurality of axially facing shoulders carried on said one of said tubular sheaths and forming a linear ratchet thereon, said shoulders extending over a major portion of the length of said one tubular sheath so as to lock said needle against movement in a direction opposite said one direction after the tip of said needle has been withdrawn into said catheter section;

locking fingers carried on said connecting element and cooperating with said shoulders to prevent said needle from moving in a reverse direction opposite said one direction through said catheter section and away from said tubular sheath at a time after the pointed end of said needle has passed into said catheter section, thus preventing inadvertent extension of said needle point back into the blood vessel while carrying particles of said catheter section at a time after said needle point has been withdrawn into the catheter section.

6. A safe intravenous catheter placement device as defined in claim 5 and further characterized as including means axially keying said first and second tubular sheaths to each other to prevent rotational movement of one sheath relative to the other.

7. A safe intravenous catheter placement device as defined in claim 5 wherein said connecting element comprises an elongated rigid shaft having one end connected to said second end of said needle and its other end connected to the said other tubular sheath.

8. A safe intravenous catheter placement device as defined in claim 5 and further characterized as including a finger gripping zone on said one tubular sheath.

9. A safe intravenous catheter placement device as defined in claim 5 wherein the point at one end of said needle is bias cut on an angle of from about 30° to about 45° with respect to the longitudinal axis of the tubular needle, and wherein the end portion of said catheter section has a bevelled tip thereon facilitating entry of the tip into a blood vessel following the point of the needle.

10. A safe intravenous catheter placement device comprising:

an elongated, tubular needle having a hollow interior and having a sharpened point at a first end thereof, and having a second end;

a tubular intravenous catheter end section positioned concentrically around a portion of said needle and including:

a first end adjacent the sharpened point at the first end of said needle, and slidably encircling the outer periphery of said needle; and an open, second end;

a protective sheath subassembly around a portion of said needle, which portion of said needle is located between the first end thereof and the second end thereof, and including the second end thereof, said protective sheath subassembly comprising:

an elongated, tubular sheath which includes at the end thereof closest to the pointed first end of said needle, a transparent cylindrical end portion encircling a medial portion of said needle between the ends of said needle and removably connected to the open, second end of said catheter end section, said tubular sheath further including:

a blood-receiving flash chamber adjacent, and communicating with, said transparent cylindrical end portion; and an elongated, tubular barrel connected to, and in coaxial alignment with, said blood-receiving flush chamber and in coaxial alignment with said cylindrical end portion for receiving within said tubular sheath a substantial portion of an elongated needle when said needle is retracted through said catheter end section and said cylindrical end portion;

a flapper valve in said flash chamber and movable from an open position allowing said needle to pass through said transparent cylindrical end portion and said catheter end section and said flash chamber, to a closed position closing said flash chamber after said needle has been retracted into said tubular sheath;

manual retraction means connected to said second end of said needle for retracting said needle through said catheter end section and cylindrical end portion into said tubular sheath so that said pointed first end is within either said flash chamber or said barrel, and said flapper valve is closed; and means for locking said needle in a position in which the pointed first end is within, and is protected by, said elongated tubular sheath.

11. A safe intravenous catheter placement device comprising:

an elongated, tubular needle having a hollow interior, and having a sharpened, pointed first end and a second end, said tubular needle having at least one radial blood flash port extending radially through the wall of said needle at a location nearer to said second end of said needle than to said first end of said needle for discharging blood passing through said needle from a blood vessel out through said radial flash port;

a tubular intravenous catheter end section positioned concentrically around a portion of said needle and including:

a first end adjacent the sharpened point at said first end of said needle and slidably encircling the outer periphery of the needle; and an open, second end;

a protective sheath subassembly around a portion of said needle, which portion of said needle is located between the first end thereof and the second end thereof, and includes the second end thereof, said protective sheath subassembly comprising:

an elongated, tubular sheath which includes, at the end thereof closest to the pointed first end of said needle;

a transparent cylindrical end portion encircling the medial portion of said needle between the ends of said needle and removably connected to the open second end of said catheter end section; and a blood-receiving flash chamber surrounding the portion of said needle having said radial blood flash port therethrough, said flash chamber being located adjacent said transparent cylindrical end portion, said elongated tubular sheath surrounding a portion of said needle which is spaced therealong from said pointed first end of said needle; and manual retracting means connected to said second end of said needle for retracting said needle through said catheter end section and said transparent cylindrical end portion of said sheath, and into said tubular sheath so that said pointed first end of said needle is within said tubular sheath, said manual retracting means comprising:

an elongated rigid rod having a first end connected to the second end of said needle, and extending in an axial direction through said tubular sheath and having a second end outside said tubular sheath; and handle means connected to said second end of said elongated rigid rod, and being accessible to manual gripping at a location outside said tubular sheath.

12. A safe intravenous catheter placement device as defined in claim 11 wherein said handle means comprises a finger ring.

13. A safe intravenous catheter placement device as defined in claim 11 wherein said handle means comprises a second tubular sheath slidably surrounding said first mentioned tubular sheath and joined to said elongated rigid rod.

14. A safe intravenous catheter placement device comprising:

an elongated, tubular needle having a hollow interior and having a sharpened, pointed first end and a second end, said tubular needle having at least one radial blood flash port extending radially through the wall of said needle at a location nearer to said second end of said needle than to said first end of said needle for discharging out through said radial flash port, blood passing through said needle from a blood vessel;

a tubular intravenous catheter end section positioned concentrically around a portion of said needle and including:

a first end adjacent the sharpened point at said first end of said needle and slidably encircling the outer periphery of the needle; and an open, second end;

a protective sheath subassembly around a portion of said needle, which portion of said needle is located between the first end thereof and the second end thereof, and includes the second end thereof, said protective sheath subassembly comprising:

an elongated, tubular sheath which includes at the end thereof closest to the pointed first end of said needle, a cylindrical end portion encircling a medial portion of said needle between the ends of said needle, and removably connected to the open end of said catheter end section, said tubular sheath further including a blood-receiving flash chamber surrounding the portion of said needle having said radial blood flash port therethrough, said flash chamber being located adjacent said cylindrical end portion, said elongated tubular sheath surrounding a portion of said needle which is spaced therealong from said pointed first end of said needle; and manual retracting means connected to said second end of said needle for retracting said needle through said catheter end section and at least partially through said cylindrical end portion, and into said tubular sheath so that said pointed first end of said needle is within said tubular sheath, said manual retracting means comprising:

an elongated tubular shaft having one of its ends connected to the second end of said tubular needle and defining a passageway communicating with the hollow interior of the needle; and handle means connected to said elongated tubular shaft and including removable cap means closing said tubular shaft at its end opposite its end connected to the second end of said needle; and means for locking said needle in a retracted, protected position in which said pointed first end is within, and is protected by, said elongated tubular sheath.

15. A safe intravenous catheter placement device comprising:

an elongated tubular hypodermic needle having a point at a sharpened first end thereof and having a second end;

a tubular intravenous catheter section positioned concentrically around said hypodermic needle and including a first end portion adjacent the tip of the hypodermic needle and snugly encircling the outer periphery of the needle, and further including an open second end; and a protective sheath subassembly connected to the second end of said needle and to the second end of said catheter section, said protective sheath subassembly comprising:

a first tubular sheath;

a second tubular sheath concentrically positioned with respect to said first tubular sheath, and slidably movable in an axial direction relative to said first tubular sheath;

one of said tubular sheaths having an end connected to said open second end of said catheter section;

a connecting element interconnecting the other of said tubular sheaths to the second end of said needle for drawing said needle in one direction through said catheter section and into the interior of said one tubular sheath when said tubular sheaths are displaced in an axial direction relative to each other; and a plurality of axially facing shoulders carried on said one of said tubular sheaths and forming a linear ratchet thereon; and locking fingers carried on said connecting element and cooperating with said shoulders to prevent said needle from moving in a reverse direction through said catheter section and away from said tubular sheath; and means axially keying said tubular sheaths to each other to permit axial relative movement therebetween while preventing rotational movement of one sheath relative to the other sheath about the common axes thereof, said axial keying means comprising:

an axially extending slot formed in one of said tubular sheaths; and a radially projecting key formed on the other of said tubular sheaths and extending into said axially extending slot to key the sheaths to each other against rotational relative movement while permitting axial movement of said two sheaths relative to each other.

16. A safe intravenous catheter placement device comprising:

an elongated tubular hypodermic needle having a point at a sharpened first end thereof and having a second end;

a tubular intravenous catheter section positioned concentrically around said hypodermic needle and including a first end portion adjacent the tip of the hypodermic needle and snugly encircling the outer periphery of the needle, and further including an open second end; and a protective sheath assembly connected to the second end of said needle and to the second end of said catheter section, said sheath subassembly comprising:

a first tubular sheath;

a second tubular sheath concentrically positioned with respect to said first tubular sheath, and slidably movable in an axial direction relative to said first tubular sheath;

one of said tubular sheaths having an end connected to said open second end of said catheter section;

means for interlocking said first and second tubular sheaths with each other against movement in either direction when said sheaths are moved relative to each other to retract said needle into the interior of said one tubular sheath and after moving said first and second tubular sheaths to an extreme axial relationship to each other so that the overall length of said first and second tubular sheaths is a maximum while retaining a portion of one telescoped around a portion of the other;

means axially keying said first and second tubular sheaths to each other to prevent rotational movement of one sheath relative to the other; and a connecting element interconnecting the other of said tubular sheaths to the second end of said needle for drawing said needle in one direction through said catheter section and into the interior of said one tubular sheath when said tubular sheaths are displaced in an axial direction relative to each other, said connecting element comprising:

an elongated rigid shaft means having one end connected to said second end of said needle, and having its other end connected to said other tubular sheath for drawing said needle through said catheter section and into the interior of said one tubular sheath;

a finger gripping zone on said one said tubular sheath; and a plurality of axially facing shoulders carried on said one tubular sheath and forming a linear ratchet thereon; and locking finger means carried on said connecting element and cooperating with said shoulders to prevent said needle from moving in a reverse direction through said catheter section and away from said tubular sheath.

* * * * *

UNITED STATES PATENT AND TRADEMARK OFFICE
CERTIFICATE OF CORRECTION

PATENT NO. : 4,944,728
DATED : July 31, 1990
INVENTOR(S) : Michael W. Carrell and Stephen H. Gericke It is certified that error appears in the above-identified patent and that said Letters Patent is hereby corrected as shown below:

In the Claims:

In Column 12, line 1, delete "bevelled" and insert -beveled-.
In Column 12, line 32, delete "flush" and insert -flash-.

Signed and Sealed this

Twelfth Day of November, 1991

Attest:

HARRY F. MANBECK, JR.

Attesting Officer    Commissioner of Patents and Trademarks